United States Patent
Haught et al.

(10) Patent No.: US 9,310,353 B2
(45) Date of Patent: Apr. 12, 2016

(54) METHOD FOR EVALUATING BIOAVAILABLE ZINC

(71) Applicant: The Procter & Gamble Company, Cincinnati, OH (US)

(72) Inventors: John Christian Haught, West Chester, OH (US); Koti Tatachar Sreekrishna, Mason, OH (US); Yakang Lin, Liberty Township, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 14/633,567

(22) Filed: Feb. 27, 2015

(65) Prior Publication Data

US 2015/0241409 A1 Aug. 27, 2015

Related U.S. Application Data

(60) Provisional application No. 61/945,437, filed on Feb. 27, 2014.

(51) Int. Cl.

| | |
|---|---|
| *G01N 33/20* | (2006.01) |
| *G01N 33/52* | (2006.01) |
| *G01N 21/64* | (2006.01) |
| *C12Q 1/02* | (2006.01) |
| *G01N 33/50* | (2006.01) |
| *G01N 33/84* | (2006.01) |
| *A61K 8/27* | (2006.01) |
| *A61Q 11/00* | (2006.01) |
| *G01N 33/58* | (2006.01) |

(52) U.S. Cl.
CPC ............... *G01N 33/502* (2013.01); *A61K 8/27* (2013.01); *A61Q 11/00* (2013.01); *G01N 33/5038* (2013.01); *G01N 33/5044* (2013.01); *G01N 33/84* (2013.01); *C12Q 1/025* (2013.01); *G01N 21/6428* (2013.01); *G01N 21/6486* (2013.01); *G01N 33/20* (2013.01); *G01N 33/5005* (2013.01); *G01N 33/5008* (2013.01); *G01N 33/582* (2013.01); *G01N 2500/10* (2013.01)

(58) Field of Classification Search
CPC .............. G01N 21/64; G01N 21/6428; G01N 21/6486; G01N 33/20; G01N 33/5005; G01N 33/5008; G01N 33/502; G01N 33/5026; G01N 33/5032; G01N 33/5044; G01N 33/582; G01N 2500/10; C12Q 1/02; C12Q 1/025
USPC ............ 436/73, 81, 164, 172; 435/4, 29, 325, 435/366; 422/82.05, 82.08
See application file for complete search history.

(56) References Cited

U.S. PATENT DOCUMENTS

| | | |
|---|---|---|
| 7,105,680 B1 | 9/2006 | O'Halloran et al. |
| 2002/0058088 A1 | 5/2002 | Henry et al. |
| 2005/0009060 A1 | 1/2005 | Bernink et al. |
| 2006/0094059 A1 | 5/2006 | Westwick et al. |
| 2008/0138298 A1 | 6/2008 | Glandorf et al. |
| 2010/0196377 A1* | 8/2010 | Jantapour et al. .......... 424/139.1 |
| 2011/0159517 A1 | 6/2011 | Gee |
| 2012/0271100 A1 | 10/2012 | Woodruff et al. |
| 2013/0243935 A1 | 9/2013 | Barnekow et al. |
| 2013/0330743 A1 | 12/2013 | Zhu |

FOREIGN PATENT DOCUMENTS

| | | |
|---|---|---|
| WO | WO9306868 | 4/1993 |
| WO | WO9408629 | 4/1994 |
| WO | WO9409056 | 4/1994 |
| WO | WO9626754 | 9/1996 |
| WO | WO0061092 | 10/2000 |
| WO | WO200556825 | 6/2005 |
| WO | WO201130108 | 3/2011 |

OTHER PUBLICATIONS

Nielsen et al. Journal of Controlled Release, vol. 60, 1999, pp. 223-233.*

Jette Jacobsen et al: "Filter-grown TR146 cells as an invitro model of human buccal epithelial permeability". European Journal of Oral Sciences, vol. 107. No. 2. Apr. 1, 1999, pp. 138-146, XP055194100. ISSN: 0909-8836, DOI: 10.1046/j.0909-8836.1999.eos107210.x p. 139-p. 145; figure 1.

Anne De Brugerolle: "SkinEthic 1-15Laboratories, a company devoted to develop and produce in vitro alternative methods to animal use", ALTEX, Jan. 2007. pp. 167-171. XP055194102. Switzerland Retrieved from the Internet: URL:http://www.altex.ch/resources/Altex 20 07 3 167 171 Brugerolle.pdf [retrieved on Jun. 8, 2015] Section 4.3 Epithelial models; p. 170; figure 1.

A. V. Gyulkhandanyan et al: "The 1-15 Zn2+-transporting Pathways in Pancreatic beta-Cells: A Role for the L-Type Voltage-Gated Ca2+ Channel". Journal of Biological Chemistry. vol. 281. No. 14. Dec. 30, 2005, pp. 9361-9372, XP055194104. ISSN: 0021-9258. DOI: 1G.1O74/jbc.M508542200 p. 9362-p. 9366; figures 1,2.

Julien Gibon et al: "The over-expression 1-15 of TRPC6 channels in HEK-293 cells favours the intracellular accumulation of zinc". Biochimica Et Biophysica Acta (BBA)—Biomembranes, Elsevier, Amsterdam. NL, vol. 1808, No. 12, Aug. 9, 2011, pp. 2807-2818. XP028316551, ISSN: 0005-2736. DOI: 10.1016/J.BBAMEM.2011. 08.013 [retrieved on Aug. 16, 2011] p. 2808-p. 2811; figures 3,4.

International Search Report and written opinion, mail date Jun. 19, 2015, 9 pages.

* cited by examiner

*Primary Examiner* — Maureen Wallenhorst

(74) *Attorney, Agent, or Firm* — James E. Oehlenschlager

(57) ABSTRACT

A method to detect bioavailable metal ions from an oral care composition and a method to select for compounds that inhibit the uptake of metal ions into cells.

17 Claims, No Drawings

METHOD FOR EVALUATING BIOAVAILABLE ZINC

FIELD OF THE INVENTION

The present invention relates to a method to detect bioavailable metal ions, such as Zinc, from an oral care composition.

BACKGROUND OF THE INVENTION

Oral care and personal health care formulations deliver molecules to the oral cavity that are not only bitter, but also astringent, for example, metal salts have a high degree of astringency and bitterness. One method of determining the level of bitterness and astringency has been through the use of cellular based assays. Buccal cells, such as TR146, have been widely used as screens for pharmaceutical uptake (H. M. Nielsen & M. R. Rassing. Int. J. Pharm. (1999) 185(2): 215-25). This cell line was derived from a squamous cell carcinoma and thus allows for continuous propagation of the cell line. The TR146 cells uptake of molecules has been used previously to determine the biological interaction with the host tissues, even though these cells are significantly different than analogous cells from healthy tissue.

Therefore, there is a need to have a cell-based assay for determining the amount of bioavailable metal ion delivered from an oral care product that uses cells or conditions more closely related to cells in the human body. Meeting such a need will allow for predicting the level of astringency an oral care product would deliver. The TR146 cells also provide a means to gauge the level of astringency in the mouth by monitoring the level of uptake of the targeted molecule. Additionally, the TR146 cells allow for monitoring the amount of soluble Zinc in an oral care formulation

SUMMARY OF THE INVENTION

A method for the detection of intracellular Zn uptake is provided that comprises providing TR146 cells; contacting Zn with the TR146 cells; adding a Zn-indicator; measuring the amount of Zn uptake within the TR146 cells.

A method for screening compounds that reduce intracellular Zn uptake is provided that comprises providing TR146 cells; adding a potential Zn uptake blocker to the TR146 cells; adding Zn to the TR146 cells; adding a Zn-indicator; measuring the amount of Zn uptake within the TR146 cells to determine if the potential Zn uptake blocker reduces Zn uptake within the TR146 cells.

A method for determining the astringency of a Zn ion containing oral care composition is provided that comprises providing TR146 cells; contacting a zinc ion containing oral care composition with the TR146 cells; adding a Zn-indicator; measuring the amount of Zn uptake within the TR146 cells.

DETAILED DESCRIPTION OF THE INVENTION

The buccal and sublingual mucosa contains an immobile expanse of smooth muscle with slow turnover of the cells. With the large number of these cells available, even minimal uptake of bioavailable or soluble metal ions would create a reservoir of ions. Due to equilibration with the oral environment, these ions are likely to be available for an extended period of time to interact with the taste cells, volatile sulfurs, and microbial flora (S. G. Singh, R. P. Singh, S. K. Gupta, R. Kalyanwat, and S. Yadav, Research J. of Pharm., Biol., and Chem., Sciences (2011) 2(3), 358-372).

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

As used herein, the word "or" when used as a connector of two or more elements is meant to include the elements individually and in combination; for example X or Y, means X or Y or both.

By "personal care composition" is meant a product, which in the ordinary course of usage is applied to or contacted with a body surface to provide a beneficial effect. Body surface includes skin, for example dermal or mucosal; body surface also includes structures associated with the body surface for example hair, teeth, or nails. Examples of personal care compositions include a product applied to a human body for improving appearance, cleansing, and odor control or general aesthetics. Non-limiting examples of personal care compositions include hair coloring compositions, oral care compositions, after shave gels and creams, pre-shave preparations, shaving gels, creams, or foams, moisturizers and lotions, cough and cold compositions, leave-on skin lotions and creams, shampoos, conditioners, shower gels, bar soaps, toilet bars, antiperspirants, deodorants, depilatories, lipsticks, foundations, mascara, sunless tanners and sunscreen lotions.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

In view of the negative sense perceptions associated with metal ions, the present invention provides one or more methods and compositions to determine the amount of bioavailable metal ions, such as Zinc (Zn). In particular, compositions and methods are provided to detect changes in extracellular and/or intracellular Zn concentration and correlate them to the ability of compositions to interrupt or block Zn uptake by cells. Further, the present disclosure generally relates to a method of evaluating bioavailable metal ions via a cell-based assay, for example through the use of the TR146 cell line, which can be used to visualize cellular uptake of Zn. The TR146 cell line is an oral cancer cell derived from the buccal mucosa, and it. Typically cancer cells have some unusual properties (as compared to somatic cells) and it was discovered by the present inventors that the TR146 cell line has enhanced Zn transport. In certain embodiments the method to detect Zn uses a dye that fluoresces in response to soluble Zn. Most cell-based assays rely on a calcium sensitive dye to determine specific cellular activity. The measure of calcium provides an indirect method of measuring cellular response levels, as compared to the present invention which directly measures changes in Zn levels, allowing for an in vitro method of predicting trends likely to occur in living tissues. The uptake into the buccal cells in a living host will likely be lower, due to saliva washout and layers of protein deposition to diffuse through. The present in vitro method provides for a means to select for compounds that inhibit metal ion uptake by cells, thus giving a read on what formulation chemistry will do to the soluble metal ion.

In certain embodiments, the present invention provides indicators and other reagents for use in detecting Zn concentrations, levels, presence, or changes thereof. In certain embodiments the present invention provides Zn-indicators. In certain embodiments, the indicators and reagents included herein provide intracellular, extracellular, or non-cellular detection and/or quantification of Zn, and/or changes in the presence or concentration of Zn, either in vivo or in vitro. In certain embodiments, the indicators described herein are capable of (1) detecting the presence of one or more Zn ions and/or Zn-containing compositions (e.g., by binding to Zn), and (2) signaling the detection of Zn ions and/or Zn-containing compositions (e.g., optically). In certain embodiments, indicators comprise one or more of: a Zn-binding group, a signaling moiety (e.g., fluorophore), and one or more linkers. In certain embodiments, a Zn-indicator comprises a Zn-binding group attached to a signaling moiety, optionally through a linker. In certain embodiments, a Zn-binding group and signaling moiety are directly attached.

In certain embodiments, the Zn-binding group comprises a chemical functionality to bind one or more Zn ions present in its local environment. In certain embodiments, upon binding a Zn ion by the Zn-binding group, a structural, conformational, chemical, physical, or other change in the Zn-indicator causes a detectable change in the signal from the signaling moiety (e.g., shift in emission maximum, shift in excitation maximum, change in intensity, etc.). In certain embodiments, detection or quantification of the signal from the signaling moiety provides a qualitative and/or quantitative means for detecting and/or measuring the presence or amount of Zn present in the indicator's local environment. In certain embodiments, detection or quantification of changes in the signal from the signaling moiety provides a qualitative and/or quantitative means for detecting and/or measuring changes in the presence or amount of Zn present in the indicator's local environment.

In certain embodiments, a Zn-indicator comprises one or more structural or functional features described in U.S. Pat. No. 7,105,680; herein incorporated by reference in its entirety.

In certain embodiments, a Zn-indicator comprises a metal-binding group. In certain embodiments, a metal binding group comprises a Zn-binding group. In certain embodiments, a Zn-indicator comprises more than one Zn-binding group (e.g., 2, 3, 4, 5, 6, 7, 8, 9, 10, etc.). In certain embodiments, a Zn-binding group is a chemical moiety capable of stably interacting with one or more Zn ions. In certain embodiments, a Zn-binding group is capable of interacting with one or more Zn ions, while covalently attached to the other functional elements of the Zn-indicator. In certain embodiments, a Zn-binding group interacts with a Zn ion through covalent and/or non-covalent binding.

The present invention is not limited to any particular type or class of Zn-binding groups. In certain embodiments, a Zn-binding group comprises a functional group capable of transiently or stably binding, coordinating, and/or chelating one or more Zn ions (e.g., free or in another complex). In certain embodiments, a Zn-binding group is Zn specific. In certain embodiments, a Zn-binding group preferentially binds Zn over other metal ions. In certain embodiments, a Zn-binding group is a general metal-binding moiety. Chemical moieties that find use as Zn-binding groups, or within Zn-binding groups, of the present invention include, but are not limited to, diethyldithiocarbamate (DEDTC), ethylenediaminetetra-acetic acid (EDTA), 1,10-phenanthroline, pyridyl-containing compounds, amine-containing compounds (e.g., tertiary amines), histidine containing compounds, sulfonamide-containing compounds, etc. In certain embodiments, a Zn-binding group has at least one functional group selected from polyalkylene oxide, hydroxylated group, or a group having at least one amine, ammonium salt, carboxylate, sulfanyl, sulfinyl, sulfonyl, phosphate, phosphonate, phosphate, tertiary amine, pyridyl group; or combinations thereof. In certain embodiments, Zn-binding groups comprise one or more sites for attachment to other functional groups within the Zn-indicator (e.g., signaling moiety, linker, another Zn-binding group, etc.).

In certain embodiments, a signaling moiety is a detectable chemical moiety. In certain embodiments, a signaling moiety is an optically detectable chemical moiety (e.g., fluorophore, chromophore, etc.). In certain embodiments, a signaling moiety comprises a fluorescent dye or fluorophore. In certain embodiments, a signaling moiety may be used as a fluorophore for detection using one or more of optical spectroscopy, fluorescence spectroscopy, confocal spectroscopy, confocal fluorescence spectroscopy, two-photon excitation (TPE) fluorescence microscopy, etc.

In certain embodiments, a signaling moiety is configured within a Zn-indicator such that coordination of one or more Zn ions by the Zn-binding group results in a detectable change in the signal from the signaling moiety. In certain embodiments, a detectable change in signal comprises a change (e.g., increase or decrease) in signal (e.g., fluorescence) intensity. In certain embodiments a detectable change (e.g., increase or decrease) in signal (e.g., fluorescence) intensity is readily detectable by a skilled artisan using the compositions and methods of the present invention (e.g., 1.1-fold . . . 1.2-fold . . . 1.5-fold . . . 2-fold . . . 5-fold . . . 10-fold . . . 20-fold . . . 50-fold . . . 100-fold . . . 200-fold . . . 500-fold . . . 1000-fold, etc.). In certain embodiments, a detectable change in signal comprises a change (e.g., increase or decrease) in the excitation maximum. In certain embodiments, a detectable change in signal comprises a change in the excitation spectrum. In certain embodiments, a detectable change in signal comprises a change (e.g., increase or decrease) in the emission maximum. In certain embodiments, a detectable change in signal comprises a change in the emission spectrum.

The present invention is not limited to any particular signaling moiety. In certain embodiments, as stated previously, the signaling moiety may be a fluorophore. The present invention is not limited to any particular fluorophore. Fluorophores and/or fluorescent labels that find use as or within signaling moieties of the present invention include, but are not limited to, e.g., fluorescein and rhodamine dyes, such as fluorescein isothiocyanate (FITC), 6-carboxyfluorescein (commonly known by the abbreviations FAM and F), 6-carboxy-2',4',7', 4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; alexa dyes, e.g., alexa fluor 555, alexa fluor 594; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes; and derivities thereof. Suitable fluorescent labels include any of the variety of fluorescent labels disclosed in U.S. Pat. No. 6,723,509, the disclosure of which is incorporated herein by reference. In certain embodiments, signaling moieties comprise one or more sites for attachment to other functional groups within the Zn-indicator (e.g., another signaling moiety, linker, Zn-binding group, etc.).

In certain embodiments of the present invention a Zn-indicator may include one or more linkers, linking moieties, linking groups, or linker regions. In certain embodiments, a linker connects two or more functional groups of a Zn-indicator (e.g., signaling moiety, Zn-binding group, etc.). In certain embodiments, a linker comprises 1-1000 atoms (e.g., 1-10, 1-100, etc.). In certain embodiments, a linker connects a signaling moiety to a Zn-binding group. In certain embodiments, one or more functional groups of a Zn-indicator (e.g., signaling moiety, Zn-binding group) may be connected to more than one other functional group of a Zn-indicator (e.g., signaling moiety, Zn-binding group) by multiple linkers. In certain embodiments, a linker is branched for connection of three or more functional groups of a Zn-indicator (e.g., signaling moiety, Zn-binding group).

The present invention is not limited to any particular linker group, as a variety of linker groups are contemplated, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (eg. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker, phospholipid derivatives, alkenyl chains, alkynyl chains, disulfide, or a combination thereof.

In certain embodiments a linker comprises a single chain connecting one functional group of a Zn-indicator (e.g., signaling moiety, Zn-binding group) to another functional group of a Zn-indicator (e.g., signaling moiety, Zn-binding group). In certain embodiments, there are multiple linkers connecting multiple Zn-binding groups to a single signaling moiety. In certain embodiments, a linker may connect multiple Zn-binding groups to each other. In certain embodiments, a linker may connect multiple signaling moieties to each other. In certain embodiments, a linker may be branched. In certain embodiments, the linker may be flexible, or rigid.

Examples of Zn-indicators include, but are not limited to FluoZin-3 (CAS#404335-95-1), RhodZin-3 (CAS#677716-65-3), FluoZin-1 (CAS#411209-53-5), and Newport Green DCF (CAS#288374-37-8).

In certain embodiments, the present invention provides methods for detection, measurement, identification, and/or quantification of Zn ions and/or Zn-containing compounds or compositions. In certain embodiments, the present invention provides methods for detection, measurement, identification, and/or quantification of Zn concentration. In certain embodiments, the present invention provides methods for detection, measurement, identification, and/or quantification of changes in Zn concentration. In certain embodiments, the present invention provides methods for correlating biological and/or cellular events, changes, processes, and/or phenomena to Zn concentration or changes thereof (e.g., extracellular Zn concentration, intracellular Zn concentration, etc.). In certain embodiments, any suitable methods of detecting and/or quantifying the presence and/or concentration of Zn ions, or changes thereof, find use in the present invention. In certain embodiments, Zn ions are detected and or quantified through the use of Zn-sensitive indicators, such as those described herein.

In certain embodiments, the present invention provides compositions and methods for the detection of Zn release and/or uptake from cells, and correlation thereof to the effectiveness of Zn uptake blockers.

Zinc uptake blockers include molecules that slow or inhibit the uptake of zinc into the TR146 cells and would allow for gauging the strength of a molecule to tie up the zinc ions. Chelants specific to zinc as demonstrated in the examples shows the effectiveness of these molecules at inhibiting zinc uptake into the cells. Therefore, the free zinc would be reduced as noted by the cell readings.

A detailed description of the invention having been provided above, the following examples are given for the purpose of illustrating the invention and are not to be construed as being a limitation on the scope of the invention or claims.

EXAMPLES

Example 1

As with most metal ions, the choice of indicator is dependent on the cell type, ion channel, and metal specificity. In the case of Zn, the specific indicator was selected by screening commercially available Zn indicators from Life Technologies, Grand Island, N.Y. TABLE 1 shows the indicators screened using TR146 cells.

To screen the Zn indicators, measurement of Zn uptake into TR146 cells was done using a FLIPR (Fluorescent Imaging Plate Reader) assay. The assay was established using a cell membrane permeable version of Zn-indicator, FluoZin-3 AM (Life Technologies, Grand Island, N.Y.). TR146 cells were grown to confluency in 15 ml growth medium [high glucose DMEM (Dulbecco's Modification of Eagle's Medium) supplemented with 10% FBS (fetal bovine serum), 100 units/ml penicillin and 100 µg/ml streptomycin in a 75 cm$^2$ flask for 3 days at 37° C. in a mammalian cell culture incubator set at 5% $CO_2$. Cells were detached with addition of 10 ml of PBS (phosphate buffered saline) and gentle hand shaking, and transferred to a 50 ml tube and centrifuged at 850 rpm for 3 minutes to remove PBS. After centrifugation, a pellet of cells was formed in the bottom of the tube separating them from the supernatant solution. The supernatant was discarded and the cell pellet suspended in 1 ml of fresh growth medium to which 5 µl (12.5 µg) of FluoZin-3 AM Zn indicator was added and incubated for 30 minutes with gentle shaking. FluoZin-3 AM is a fluorescent dye used for quantifying intracellular Zn concentrations in the 1 to 100 nM to range. At the end of the 30 minutes, 45 ml of assay buffer [1×HBSS (Hank's Balanced Salt Solution), 20 mM HEPES (4-(2-Hydroxyethyl)-1-piperazineethanesulfonic acid)] was added to wash the cells and the resulting combination was then centrifuged at 850 rpm for 3 minutes to remove excess buffer and FluoZin-3

AM Zn indicator. The pelleted cells were re-suspended in 10 ml assay buffer and 90 µl aliquots (~50,000 cells) per well delivered to a 96-well assay plate and the plate was placed into a fluorometric imaging plate reader (FLIPR384 from Molecular Devices, Sunnyvale, Calif.) and basal fluorescence recorded (excitation wave length 494 nm and emission wave length 516 nm). Then Zn salt (for example Zn-lactate) was added and the increase in fluorescence was recorded for 5 minutes.

TABLE 1

| Dye | Affinity $K_d$ ($Zn^{2+}$) and fold increase in fluorescence |
|---|---|
| FluoZin-3 | 15 nM (>50-fold increase in fluorescence in response to saturating levels of $Zn^{2+}$) |
| RhodZin-3 | 65 nM (>50-fold increase in fluorescence in response to saturating levels of $Zn^{2+}$) |
| FluoZin-1 | 8 uM |
| Newport Green DCF | 30 uM |

The FluoZin-3 and RhodZin-3 were found to have the most affinity for the flux of Zn into the TR146 cell line. FluoZin-3 was used for the data reported herein.

Example 2

Flux of Zn Salts in TR146

Measurement of Zn uptake into TR146 cells was done using a FLIPR (Fluorescent Imaging Plate Reader) assay. The assay was established using a cell membrane permeable version of Zn dye, FluoZin-3 AM (Life Technologies, Grand Island, N.Y.). TR146 cells were grown in 15 ml growth medium [high glucose DMEM (Dulbecco's Modification of Eagle's Medium) supplemented with 10% FBS (fetal bovine serum), 100 units/ml penicillin and 100 µg/ml streptomycin in a 75 cm² flask for 3 days at 37° C. in a mammalian cell culture incubator set at 5% CO2. Cells were detached with addition of 10 ml of PBS (phosphate buffered saline) and gentle hand shaking, and transferred to a 50 ml tube and centrifuged at 850 rpm for 3 minutes to remove PBS. After centrifugation, a pellet of cells was formed in the bottom of the tube separating them from the supernatant solution. The supernatant was discarded and the cell pellet suspended in 1 ml of fresh growth medium to which 5 µl (12.5 µg) of FluoZin-3 AM Zn indicator was added and incubated for 30 minutes with gentle shaking. FluoZin-3 AM is a fluorescent dye used for quantifying intracellular Zn concentrations in the 1 to 100 nM to range. At the end of the 30 minutes, 45 ml of assay buffer [1×HBSS (Hank's Balanced Salt Solution), 20 mM HEPES (4-(2-Hydroxyethyl)-1-piperazineethanesulfonic acid)] was added to wash the cells and the resulting combination was then centrifuged at 850 rpm for 3 minutes to remove excess buffer and FluoZin-3 AM Zn indicator. The pelleted cells were re-suspended in 10 ml assay buffer and 90 µl aliquots (~50,000 cells) per well delivered to a 96-well assay plate and the plate is placed into a fluorometric imaging plate reader (FLIPR384 from Molecular Devices, Sunnyvale, Calif.) and basal fluorescence recorded (excitation wave length 494 nm and emission wave length 516 nm). Then Zn salt (for example Zn-lactate) was added and the increase in fluorescence was recorded for 5 minutes. Zn-flux observed with different Zn salts with Zn-lactate value as reference (100%) is shown below in TABLE 2.

TABLE 2

| Zn Salt | Concentration | Fluorescence Unit | % of Zn Lactate Flux |
|---|---|---|---|
| ZnGlycinate | 4.40% | 41086.61 | 86.93 |
| ZnCl2 | 1 mM | 47853.41 | 101.25 |
| ZnSO4 | 1 mM | 47853.41 | 101.25 |
| ZnPhosphate | Saturated | 49686.65 | 105.13 |
| ZnOxalate | Saturated | 55389.93 | 117.2 |
| ZnAcetate | 10 uM | 48547.79 | 102.72 |
| ZnOxide | Saturated | 50391.21 | 106.62 |
| ZnPyrithione | 10 mM | 50467.87 | 106.78 |
| Water | | 1901.26 | 4.02 |

TABLE 2 shows the effects of Zn salts with varying counterions with respect to the flux of the Zn ion into the TR146 cells. Zn glycinate showed less Zn flux (86.93% of Zn Lactate flux) than did the other salts. This illustrates that the cells can differentiate the varying solubilities of zinc due to the counter ion or chelant. Even at 4.4% which is 206 mM, Zn flux is slower than what is seen with other Zn salts at much lower concentrations Example 3

Initial Testing of Polyquats to Block Zn Uptake into TR146 Cells

TR146 buccal mucosal cells, obtained from Cancer Research Technologies Ltd., U.K., were propagated in a 75 cm² flask by using a whole vial of cells (approximately 1 ml) as provided by Cancer Research Technologies Ltd. in Dulbecco's modified Eagle medium (DMEM) high glucose (Life Technologies, Grand Island, N.Y.). The culture medium supplemented with 3.7 mg/ml NaHCO₃, 10% FCS, 50 units/ml penicillin G, and 50 mg/ml streptomycin sulphate. Cells were passaged when 90% confluence was reached. The medium was discarded, and cells were washed twice with sterile DPBS (without calcium and magnesium, Mediatech, Inc., Manassas, Va.) and 0.25% trypsin-EDTA solution (Life Technologies, Grand Island, N.Y.) was added. A 75 cm² flask was placed at 37° C. for 10 minutes and then detached cells were suspended in growth medium and seeded in 96 well micro-titer plate.

The procedure for testing Zn uptake and its blocking by the polyquats was performed as described in EXAMPLE 2.

TABLE 3

| Cationic Polymer | Final test dose of quat + 10 µM Zn-lactate | Fluorescent Counts with no Zn | Fluorescent counts with Zn | % Reduction compared to Zn control |
|---|---|---|---|---|
| Mirapol 100 CAS# 26062-79-3 (Polyquaternium-6) | 0.17% | 62.3 | 1877 | −5.84% (enhances Zn uptake) |
| Mirapol A-15 CAS# 68555-36-2 (Polyquaternium-2) | 0.17% | 37.3 | 1157.7 | 12.4% |

TABLE 3-continued

| Cationic Polymer | Final test dose of quat + 10 μM Zn-lactate | Fluorescent Counts with no Zn | Fluorescent counts with Zn | % Reduction compared to Zn control |
|---|---|---|---|---|
| Merquat ® 2200 CAS# 26590-05-6 (Polyquaternium-7) | 0.17% | 42.7 | 1645.7 | 7.4% |
| Hypan ® QT100 CAS# 136505-02-7 (Polyquaternium-31) | 0.02% | 169 | 2153.3 | −21.6% (enhances Zn uptake) |
| Luviquat ® FC550 CAS# 95144-24-4 (Polyquaternium-16) | 0.17% | 41.7 | 1851 | −4.4% (enhances Zn uptake) % |
| Luviquat ® FC905 CAS# 95144-24-4 (Polyquaternium-16) | 0.17% | 47.7 | 1879.7 | −7.0% (enhances Zn uptake) |
| Luviquat ® Care Plymer CAS# 150599-70-5 (Polyquaternium-44) | 0.17% | 50.7 | 1630 | 8.3% |
| Ucare ™ Polymer JR-125 CAS# 81859-24-7 (Polyquaternium-10) | 0.17% | 54.33 | 1851 | −4.36% (enhances Zn uptake) |
| Ucare ™ Polymer JR-30M CAS# 81859-24-7 (Polyquaternium-10) | 0.02% | 46.7 | 1739.3 | 2.0% |
| Ucare ™ Polymer JR-400 CAS# 81859-24-7 (Polyquaternium-10) | 0.08% | 55.3 | 1797.7 | 1.3% (enhances Zn uptake) |
| Ucare ™ Polymer LK CAS# 81859-24-7 (Polyquaternium-10) | 0.08% | 46.3 | 1869 | 5.4% (enhances Zn uptake) |
| Softcat Polymer SL-5 CAS# 68610-92-4 (Polyquaternium-67) | 0.02% | 61.7 | 1690.3 | 4.8% |
| Softcat Polymer SL-30 CAS# 68610-92-4 (Polyquaternium-67) | 0.02% | 17.7 | 1854.7 | 4.6% (enhances Zn uptake) |
| Water control | na | 27 | 1770.7 | 0 |
| Control Zn lactate | na | 24.5 | 1774.8 | 0 |

Of the polyquats shown in TABLE 3, only Mirapol A-15 showed >10% blocking of Zn uptake into the TR146 cells. When this protocol was applied to fully formulated dentifrices, the level of bioavailable Zn could be readily observed, as shown in TABLE 2.

Example 4

Bioavailability of Zn from Formulated Dentifrices

SAMPLES A, B, C, D having the components shown below in TABLE 4, were tested to determine the effect of Zn chelation on Zn uptake.

TABLE 4

| | Samples | | | |
|---|---|---|---|---|
| | Dentifrice | | Rinse | |
| Component | A | B | C | D |
| FD&C Blue #1 Color Solution | — | — | 0.0005% | 0.0005% |
| Polyethylene Specs, blue | 0.35% | 0.1% | — | — |
| Sodium Fluoride | 0.234% | — | — | — |
| Stannous Fluoride | — | 0.454 | — | — |
| CARBOMER 956 | — | — | — | — |
| Poloxamer 407 | — | 0.1% | 0.001% | 0.06% |
| Sodium Saccharin | 0.4% | 0.8% | 0.013% | 0.025% |
| Sucralose | — | — | 0.008% | 0.015% |
| Sodium Citrate Dihydrate | 0.274% | — | — | — |
| Zn Citrate Dihydrate | 0.788% | — | — | — |
| Zn Lactate | — | 2.0% | 0.05% | — |
| Stannous Chloride Dihydrate | 0.209% | — | — | — |
| Mica, Titanium Dioxide Coated | 0.4% | — | — | — |
| Sodium Gluconate | — | 1.064% | — | — |
| Hydroxyethycellulose | 0.3% | 1.0% | — | — |
| Peppermint Flavor | 1.25% | — | 0.1% | — |
| Wintergreen Flavor | — | 1.1% | — | 0.12% |
| Cetylpyridinium Chloride | — | — | 0.074% | 0.074% |
| Glycerin | — | — | 18% | 5.0% |
| Carboxymethylcellulose Sodium | 1.3% | 1.3% | — | — |
| Carregeenan Mixture IOTA | 0.7% | 0.7% | — | — |
| Gantrez S-95 (35% solution) | — | 5.71% | — | — |
| Sodium Lauryl Sulfate 28% Solution | 1.0% | 5.0% | — | — |
| Silica, Dental Type, NF (Zeodent 119) | 17.0% | — | — | — |
| Fused Silica (Tecosil 10) | — | 15.0% | — | — |
| Sorbitol Solution | 40.5% | 36.3% | — | — |
| Xylitol | — | 3.0% | — | — |
| Methylparaben | — | — | 0.02% | 0.02% |
| Propylparaben | — | — | 0.005% | 0.005% |
| Sodium Hydroxide | — | 1.34% | — | — |

TABLE 4-continued

| | Samples | | | |
|---|---|---|---|---|
| | Dentifrice | | Rinse | |
| Component | A | B | C | D |
| Water Purified, USP, PhEur, JP, JSCI | QS | QS | QS | QS |

The dentifrice samples (SAMPLES A and B) were 0.1 gram/1 ml DMSO extracted and DMSO extract diluted 40 fold in growth medium; rinse samples (SAMPLES C and D) were diluted directly in growth medium. 20 μl of each sample was added to 100 ul cells (approximately 10,000 cells) high glucose DMEM (Dulbecco's Modification of Eagle's Medium) supplemented with 10% FBS (fetal bovine serum), Penicillin/streptomycin (100 units/ml penicillin and 100 μg/ml streptomycin. Measurement of Zn uptake into TR146 cells was done using a FLIPR (Fluorescent Imaging Plate Reader) assay, as described in EXAMPLE 2.

SAMPLES A, B, C, D (shown in TABLE 4), shows that increasing chelation of Zn can be determined by the flux through the TR146 cells, as the lower the value in TABLE 5, equals less zinc available for flux, thus indicating a stronger chelant. The importance of this method is in the ability to provide an in vitro method that can predict how the formula components will behave in vivo, specifically the Zn and its subsequent availability for tartar removal, breath reduction, and antimicrobial activity.

TABLE 5

| 0.01% Dentifrices A-D tested on the TR146 Cells | % of Zn Lactate Control (% Zn uptake by TR146 cells) |
|---|---|
| A (contains 0.788% Zn Citrate) | 81.37% |
| B (contains 2% Zn Lactate) | 56.43% |
| C (contains Zn Lactate) | 23.07% |
| D (contains no Zn) | 5.43% |
| Water Blank | 4.02% |
| Zn Lactate Control | 100% |

Sample dentifrice B and C showed less Zn uptake than the control Zn lactate. Sample B's reduced Zn uptake is likely due to the chelant (sodium gluconate) in the dentifrice. These results indicate the lack of bioavailable Zn, as shown by the reduced amount of Zn uptake in Samples B, C, and D. This may affect the end benefit of the Zn, whether it's targeted towards tartar removal or reduction of bad breath. This in vitro method therefore provides a means to optimize formulations, either for highly bioavailable Zn or lack thereof, without having to do human testing as the first read on a formulation's Zn efficacy. SAMPLE D and the water blank show background noise of the measuring process ((5.43% and 4.02% respectively).

Example 5

Chelant Effects on Zn Flux Via TR146 Measurements

TABLE 6 shows the effects of the combinations of chelants and zinc. 50 μM of each chelant was combined with 50 μM of zinc lactate, as shown in the $3^{rd}$ column in TABLE 6. 5 μM of each of the chelants was combined with 5 μM zinc lactate, as shown in column four of TABLE 6. These combinations were then placed into growth media and measurement of Zn uptake into TR146 cells was done using a FLIPR (Fluorescent Imaging Plate Reader) assay, as described in EXAMPLE 2. The controls, the chelant alone at either 50 or 5 μM was shown in columns 5 and 6 respectively, to show the chelant did not elicit a fluorescent response.

TABLE 6

| Chelant | Zn Only | 50 micro M Chelant + 50 micro M Zn lactate | 5 micro M Chelant + 5 micro M Zn lactate | 50 micro M Chelant Control | 5 micro M Chelant Control |
|---|---|---|---|---|---|
| No Chelant Zn Only Control (50 micro M Zn Lactate) | 100%* | | | | |
| Sodium Hexametaphosphate | | 63.81%* | 105.02% | 0.00% | NA |
| Sodium acid pyrophosphate | | 0.00% | 82.87% | 0.00% | 0.00% |
| Sodium tripolyphosphate | | 0.00% | 92.99% | 0.00% | 0.00% |
| Sodium D-gluconate | | 112.99% | 101.31% | 0.00% | 1.51% |
| Sodium citrate | | 43.63% | 104.83% | 0.00% | 0.00% |
| Carbopol 956 polymer | | 71.46% | 105.74% | 5.58% | 3.15% |
| Phytic acid | | 33.87% | 20.07% | 0.00% | 0.00% |
| Gantrez S-95 | | 103.21% | 108.67% | 0.00% | 1.41% |

*All percentages are relative the flux of the Zn lactate control.

TABLE 6 showed the effects of high Zn chelation as measured by flux into the TR146 cells. The strong chelants for Zn, such as sodium acid pyrophosphate and sodium tripolyphosphate at 50 μM did not allow for any measureable levels of Zn to be detected in the TR146 cell fluorescent system.

Example 6

Chelant Effects on Bioavailable Zn

TABLE 7 shows the effects of various cationic polymers and dentifrice binders upon the uptake of 50 μM zinc lactate by the TR146 cells. These materials were combined with the zinc lactate and placed into the growth media of the TR146 cells prior to the introduction of the dye, as described in EXAMPLE 2.

TABLE 7

| Chelant | Fluorescence Units (percentage of zinc lactate) |
|---|---|
| 50 μM Zn Lactate | 100% |
| 1% Lupamine + 50 μM Zn Lactate | 0 |
| 1% Lupasol + 50 μM Zn Lactate | 0 |
| 1% Polyethylene oxide + 50 μM Zn Lactate | 21.68 |

TABLE 7-continued

| Chelant | Fluorescence Units (percentage of zinc lactate) |
|---|---|
| 1% CM-cellulose (China) + 50 μM Zn Lactate | 81.36 |
| 1% Hydroxyethyl cellulose + 50 μM Zn Lactate | 35.13 |
| 1% Xanthan gum + 50 μM Zn Lactate | 38.61 |
| 1% Carbopol + 50 μM Zn Lactate | 17.01 |
| 1% poloxmer 407 + 50 μM Zn Lactate | 86.38 |
| 1% PVP + 50 μM Zn Lactate | 76.64 |

Example 7

Competitive Inhibition from Amine Polymers

TABLE 8 shows the combination of amine polymers, in combination with zinc chloride. The polymers were combined with the zinc chloride (polymer and Zn combinations in 20 ul of growth media were mixed with TR146 cells (approximately 10,000 in 100 μl growth media)) into the growth media of the TR146 cells prior to the introduction of the dye, as described in EXAMPLE 2.

TABLE 8

| ZnCl2 complex | Zn Flux as a percentage of the Zn Chloride Control |
|---|---|
| Lupamine (0.005%) + ZnCl2 (140 uM) | 80.48% |
| Lupasol (0.005%) + ZnCl2 (140 uM) | 24.92% |
| Lupamine (0.005%) + ZnCl2 (140 uM); surfactant + ethanol | 89.25% |
| Lupasol (0.005%) + ZnCl2 (140 uM); surfactant + ethanol) | 11.31% |
| Lupamine (0.005%) | 0 |
| Lupasol (0.005%) | 0 |
| ZnCl2 (140 uM) | 100% |

TABLE 8 shows the effects of polymers with primary, secondary, and tertiary amines, which can be protonated at varying pH's. The effects of which may serve to provide cationinc charge repulsion, thus preventing the bioavailable Zn from entering the TR146 cells. The effect of the Lupasol materials was a clear inhibition of the Zn flux, where the Lupamine's showed only marginal Zn flux reduction.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Method for the detection of intracellular Zn uptake comprising:
    providing TR146 cells;
    contacting Zn with the TR146 cells;
    adding a Zn-indicator having a Zn-binding group and a signaling moiety, wherein the signaling moiety comprises a detectable chemical moiety;
    measuring the amount of Zn uptake within the TR146 cells, by detecting the signaling chemical moiety of the Zn-indicator within the TR146 cells.

2. The method of claim 1, wherein the Zn-indicator comprises linker.

3. The method of claim 1, wherein the Zn-binding group comprises a functional group capable of at least one of transiently binding, stably binding, coordinating, or chelating one or more Zn ions.

4. The method of claim 3, wherein the Zn-binding group comprises at least one of diethyldithiocarbamate (DEDTC), ethylenediaminetetra-acetic acid (EDTA), 1,10-phenanthroline, pyridyl-containing compound, amine-containing compound, histidine containing compound, or sulfonamide-containing compound.

5. The method of claim 3, wherein the Zn-binding group comprises at least one of polyalkylene oxide, hydroxylated group, ammonium salt, carboxylate, sulfanyl, sulfinyl, sulfonyl, phosphate, phosphonate, tertiary amine, or pyridyl group.

6. The method of claim 1, wherein the signaling moiety comprises at least one of a fluorescent dye or fluorophore.

7. The method of claim 6, wherein the signaling moiety comprises at least one of fluorescein dye, rhodamine dye, cyanine dye, alexa dye, benzimide dye, ethidium dye, acridine dye, carbazole dye, phenoxazine dye; porphyrin dye, polymethine dye, cyanine dye, or quinoline dye.

8. Method for screening compounds that reduce intracellular Zn uptake comprising:
    providing TR146 cells;
    contacting Zn with the TR146 cells;
    adding a Zn-indicator having a Zn-binding group and a signaling moiety, wherein the signaling moiety comprises a detectable chemical moiety;
    measuring the amount of Zn uptake within the TR146 cells, by detecting the signaling chemical moiety of the Zn-indicator within the TR146 cells;
    providing TR146 cells;
    adding a potential Zn uptake blocker to the TR146 cells;
    adding Zn to the TR146 cells;
    adding a Zn-indicator having a Zn-binding group and a signaling moiety, wherein the signaling moiety comprises a detectable chemical moiety;
    measuring the amount of Zn uptake within the TR146 cells, by detecting the signaling chemical moiety of the Zn-indicator within the TR146 cells, to determine if the potential Zn uptake blocker reduces Zn uptake within the TR146 cells.

9. The method of claim 8, wherein the Zn-indicator comprises a linker.

10. The method of claim 8, wherein the Zn-binding group comprises a functional group capable of at least one of transiently binding, stably binding, coordinating, or chelating one or more Zn ions.

11. The method of claim 8, wherein the signaling moiety comprises at least one of a fluorescent dye or fluorophore.

12. The method of claim 11, wherein the signaling moiety comprises at least one of fluorescein dye, rhodamine dye, cyanine dye, alexa dye, benzimide dye, ethidium dye, acridine dye, carbazole dye, phenoxazine dye; porphyrin dye, polymethine dye, cyanine dye, or quinoline dye.

13. Method for determining the astringency of a Zn ion containing oral care composition comprising:
    providing TR146 cells;
    contacting a zinc ion containing oral care composition with the TR146 cells;
    adding a Zn-indicator having a Zn-binding group and a signaling moiety, wherein the signaling moiety comprises a detectable chemical moiety;
    measuring the amount of Zn uptake within the TR146 cells, by detecting the signaling chemical moiety of the Zn-indicator within the TR146 cells.

14. The method of claim 13, wherein the oral care composition comprises at least one of a dentifrice, mouth rinse, mousse, foam, mouth spray, lozenge, chewable tablet, chewing gum, tooth whitening strips, floss, floss coatings, breath freshening dissolvable strips, denture care, or denture adhesive product.

15. The method of claim 13, wherein the Zn-indicator comprises a linker.

16. The method of claim 13, wherein the Zn-binding group comprises a functional group capable of at least one of transiently binding, stably binding, coordinating, or chelating one or more Zn ions.

17. The method of claim 13, wherein the signaling moiety comprises at least one of a fluorescent dye or fluorophore.

* * * * *